United States Patent
Xie et al.

(10) Patent No.: US 11,209,381 B2
(45) Date of Patent: Dec. 28, 2021

(54) MEDICAL DETECTION SUBSTRATE AND MANUFACTURING METHOD THEREOF, MEDICAL DETECTION CHIP AND MEDICAL DETECTION SYSTEM

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Zhenyu Xie, Beijing (CN); Zhenyu Hao, Beijing (CN); Yuekai Gao, Beijing (CN); Lijun Mao, Beijing (CN); Tiansheng Li, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 486 days.

(21) Appl. No.: 16/308,221

(22) PCT Filed: Feb. 2, 2018

(86) PCT No.: PCT/CN2018/075012
§ 371 (c)(1),
(2) Date: Dec. 7, 2018

(87) PCT Pub. No.: WO2019/015302
PCT Pub. Date: Jan. 24, 2019

(65) Prior Publication Data
US 2021/0223199 A1    Jul. 22, 2021

(30) Foreign Application Priority Data
Jul. 20, 2017 (CN) .......................... 201710595582.6

(51) Int. Cl.
*G01N 27/327* (2006.01)

(52) U.S. Cl.
CPC .................................. *G01N 27/327* (2013.01)

(58) Field of Classification Search
None
See application file for complete search history.

(56) References Cited

U.S. PATENT DOCUMENTS 5,066,372 A * 11/1991 Weetail .............. G01N 27/3271
506/4
7,833,396 B2    11/2010 Fukushima
(Continued)

FOREIGN PATENT DOCUMENTS

| CN | 101004411 A | 7/2007 |
| CN | 101669025 A | 3/2010 |
| CN | 106249973 A | 12/2016 |

OTHER PUBLICATIONS

International Search Report of PCT/CN2018/075012 in Chinese, dated May 3, 2018 with English translation.
(Continued)

*Primary Examiner* — J. Christopher Ball
(74) *Attorney, Agent, or Firm* — Collard & Roe, P.C.

(57) ABSTRACT

A medical detection substrate and a manufacturing method thereof, a medical detection chip and a medical detection system are provided. The medical detection substrate includes: a substrate, and a detection unit on the substrate; the detection unit includes two groups of test electrodes, the substrate includes a plurality of recessed portions, and the at least two groups of test electrodes are located in the plurality of recessed portions and spaced apart by insulation bank portions. The two groups of test electrodes are insulated and spaced apart by the insulation bank portions, so as to effectively avoid a transverse interference electric field to be generated between the two groups of test electrodes, thereby
(Continued)

effectively improving the detection accuracy and sensitivity of the medical detection substrate, and providing a reliable basis for disease diagnosis.

18 Claims, 12 Drawing Sheets

(56) References Cited

U.S. PATENT DOCUMENTS

2010/0052080 A1   3/2010   Tello et al.
2015/0253274 A1   9/2015   Lee et al.

OTHER PUBLICATIONS

Notice of Transmittal of the International Search Report of PCT/CN2018/075012 in Chinese, dated May 3, 2018.
Written Opinion of the International Searching Authority of PCT/CN2018/075012 in Chinese, dated May 3, 2018 with English translation.
Chinese Office Action in Chinese Application No. 201710595582.6, dated Jun. 6, 2019 with English translation.

* cited by examiner

MEDICAL DETECTION SUBSTRATE AND MANUFACTURING METHOD THEREOF, MEDICAL DETECTION CHIP AND MEDICAL DETECTION SYSTEM

CROSS REFERENCE TO RELATED APPLICATIONS

This application is the National Stage of PCT/CN2018/075012 filed on Feb. 2, 2018, which claims priority under 35 U.S.C. § 119 of Chinese Application No. 201710595582.6 filed on Jul. 20, 2017, the disclosure of which is incorporated by reference.

TECHNICAL FIELD

The present disclosure relates to a medical detection substrate and a manufacturing method thereof, a medical detection chip and a medical detection system.

BACKGROUND

In recent years, genetic testing is being gradually developed with the rapid development of the gene sequencing market, and the cost of genetic testing has also been greatly reduced. However, the cost for testing the whole genome of the human body is still unacceptable, and the popularity of detection on some major diseases is still relatively low. Therefore, there is an urgent need for genetic testing for mainstream diseases in the market, for example, the detection of some mainstream cancers appears to be particularly important. A liquid biopsy chip is a newly developed technology, it does not need to detect the whole genome to diagnose the disease, but directly collects a part of the body fluid of the human body to complete the test, which not only saves the testee from suffering, but also does not require the testee to pay much on detection, thereby allowing disease detection to be simple and quick.

SUMMARY

An embodiment of the present disclosure provides a medical detection substrate, including: a substrate, and a detection unit located on the substrate, the detection unit includes at least two groups of test electrodes, the substrate includes a plurality of recessed portions, the at least two groups of test electrodes are located in the plurality of recessed portions and spaced apart by insulation bank portions.

In some examples, the plurality of recessed portions are located in the substrate.

In some examples, the medical detection substrate further includes an insulation layer located between the substrate and the detection unit, the plurality of recessed portions are located in the insulation layer.

In some examples, each group of the at least two groups of test electrodes includes at least one test electrode, each test electrode includes a plurality of test sub-electrodes connected in series, and the plurality of test sub-electrodes are located in the plurality of recessed portions.

In some examples, the plurality of test sub-electrodes connected in series in each test electrode are electrically connected by wires.

In some examples, the plurality of recessed portions are in a one-to-one correspondence with the test electrodes, the plurality of test sub-electrodes and the wires are located in the plurality of recessed portions; or, the plurality of recessed portions are in a one-to-one correspondence with the test sub-electrodes, at least a part of the wires between adjacent ones of the test sub-electrodes is located on the bank portions between the plurality of recessed portions.

In some examples, each group of the at least two groups of test electrodes includes at least two test electrodes, the at least two test electrodes in each group of the at least two groups of test electrodes are electrically connected with each other.

In some examples, the test electrodes in the at least two groups of test electrodes are alternately arranged.

In some examples, a depth of each of the plurality of recessed portions is greater than a thickness of each of the plurality of test sub-electrodes.

In some examples, the depth of each of the plurality of recessed portions is between 10 microns and 100 microns; the thickness of each of the plurality of test sub-electrodes is between 100 nm and 500 nm.

In some examples, each of the plurality of test sub-electrodes has a sheet resistance ranging from 10Ω/□ to 200Ω/□.

In some examples, each of the plurality of test sub-electrodes is made of indium tin oxide or inert metal.

In some examples, the medical detection substrate further includes: a plurality of data lines respectively electrically connected with the at least two groups of test electrodes in the detection unit, each of the plurality of data lines is made of at least two metal materials arranged in a layer stacked manner, and the data line is configured to transmit a detection signal outputted by the detection unit.

In some examples, the medical detection substrate further includes: a DNA target substrate located above the at least two groups of test electrodes and a DNA paired target located above the DNA target substrate.

Another embodiment of the present disclosure provides a medical detection chip, which includes the medical detection substrate according to any one of the examples and a labeled detection reagent located on the medical detection substrate.

Another embodiment of the present disclosure provides a medical detection system, including: the medical detection chip as mentioned above, and a signal processing unit configured to process a detection signal outputted by the detection unit in the medical detection chip.

Another embodiment of the present disclosure provides a manufacturing method of a medical detection substrate, including: forming a plurality of recessed portions on a substrate; and forming at least two groups of test electrodes in the plurality of recessed portions, the at least two groups of test electrodes being spaced apart by insulation bank portions between the plurality of recessed portions.

In some examples, the method further includes: before forming the plurality of recessed portions on the substrate, forming an insulation layer on the substrate, the plurality of recessed portions are formed in the insulation layer.

In some examples, a height of each of the bank portions is greater than or equal to that of each of the test electrodes by taking a plane on which a bottom surface of the test electrode is located as a reference.

BRIEF DESCRIPTION OF THE DRAWINGS

In order to clearly illustrate the technical solution of embodiments of the present disclosure, the drawings of the embodiments will be briefly described in the following, it is obvious that the drawings in the description are only related

DETAILED DESCRIPTION

In order to make objects, technical details and advantages of the embodiments of the present disclosure apparently, the technical solutions of the embodiments will be described in a clearly and fully understandable way in connection with the drawings related to the embodiments of the present disclosure. It is obvious that the described embodiments are just a part but not all of the embodiments of the present disclosure. Based on the described embodiments herein, a person having ordinary skill in the art may obtain other embodiment(s), without any inventive work, which should be within the scope of the present disclosure.

Figure 1:
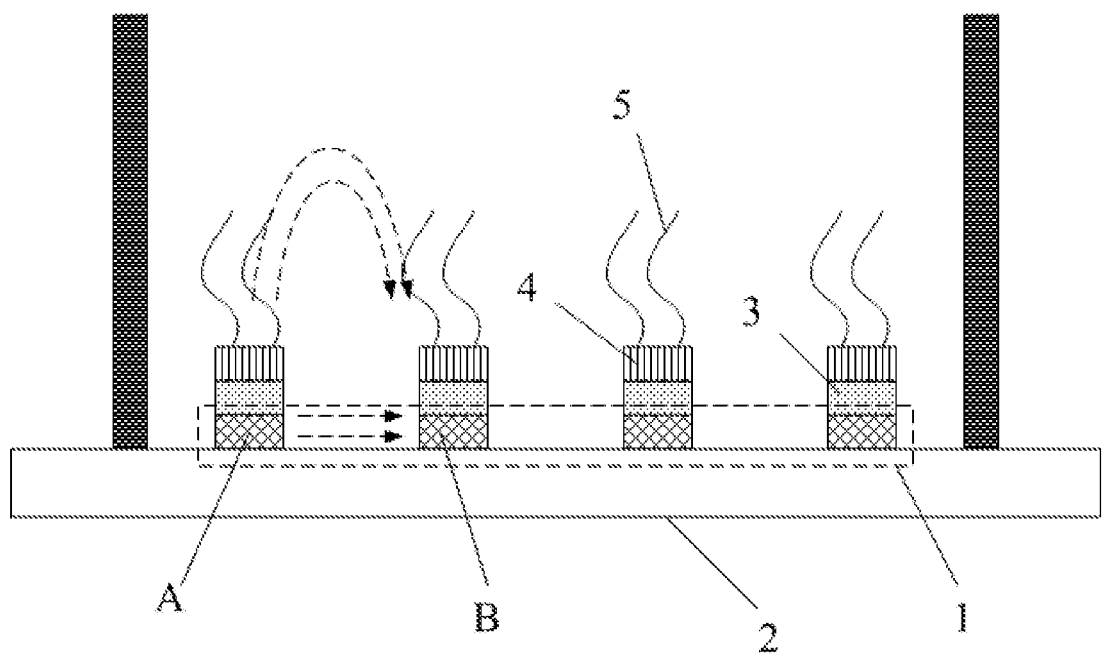
FIG. 1 is a sectional view of a liquid biopsy chip in an existing art.

FIG. 1 illustrates a sectional view of a liquid biopsy chip. As illustrated in FIG. 1, detection units 1 (in a dotted border) and a data line (not illustrated in FIG. 1) are both located on a substrate 2, each of the detection units 1 includes two groups of test electrodes, and each group of the two groups of test electrodes includes a plurality of test sub-electrodes. For example, A refers to a test sub-electrode in a first group of test electrodes, and B refers to a test sub-electrode in a second group of test electrodes. A conductive layer 3, a DNA target substrate 4 and a DNA paired target 5 are sequentially formed on each test sub-electrode in the detection unit 1. A biopsy chip is obtained after the detection unit 1 is packaged. In an actual application process, liquid to be detected needs to be poured into the detection unit 1 which has been packaged, and ions are released after a target DNA in the liquid to be detected is paired with the DNA paired target, so that the liquid to be detected is changed from an insulation state into a conductive state, thereby generating an electric current between the two groups of test electrodes, and determining a type of disease by detecting the magnitude of the electric current.

However, because A and B are in the same plane, as illustrated in FIG. 1, there is not only a bending interference electric field on a surface of A and B (as illustrated by the curved dotted arrows), but also a transverse interference electric field (as illustrated by the transverse dashed arrows). The two interference electric fields will affect the flow of ions in the liquid to be detected, which in turn affect the electric current between the two groups of test electrodes, and affect the test result. Moreover, because a distance between A and B is small, the transverse interference electric field between A and B is much greater than the bending interference electric field, that is, the interference caused by the transverse interference electric field on the ion flow in the liquid to be detected is much greater than the interference caused by the bending interference electric field on the ion flow in the liquid to be detected. Therefore, avoiding the transverse interference electric field to be generated between A and B becomes a key to improve the detection accuracy.

Generally, the transverse interference electric field can be reduced by thinning a thickness of A and B, however, because A and B are still in the same plane, the transverse interference electric field cannot be completely eliminated by way of thinning Based on this, how to effectively eliminate the transverse interference electric field between A and B, and improve the accuracy and sensitivity of disease detection is a technical problem that needs to be solved by those skilled in the art.

Figure 2:
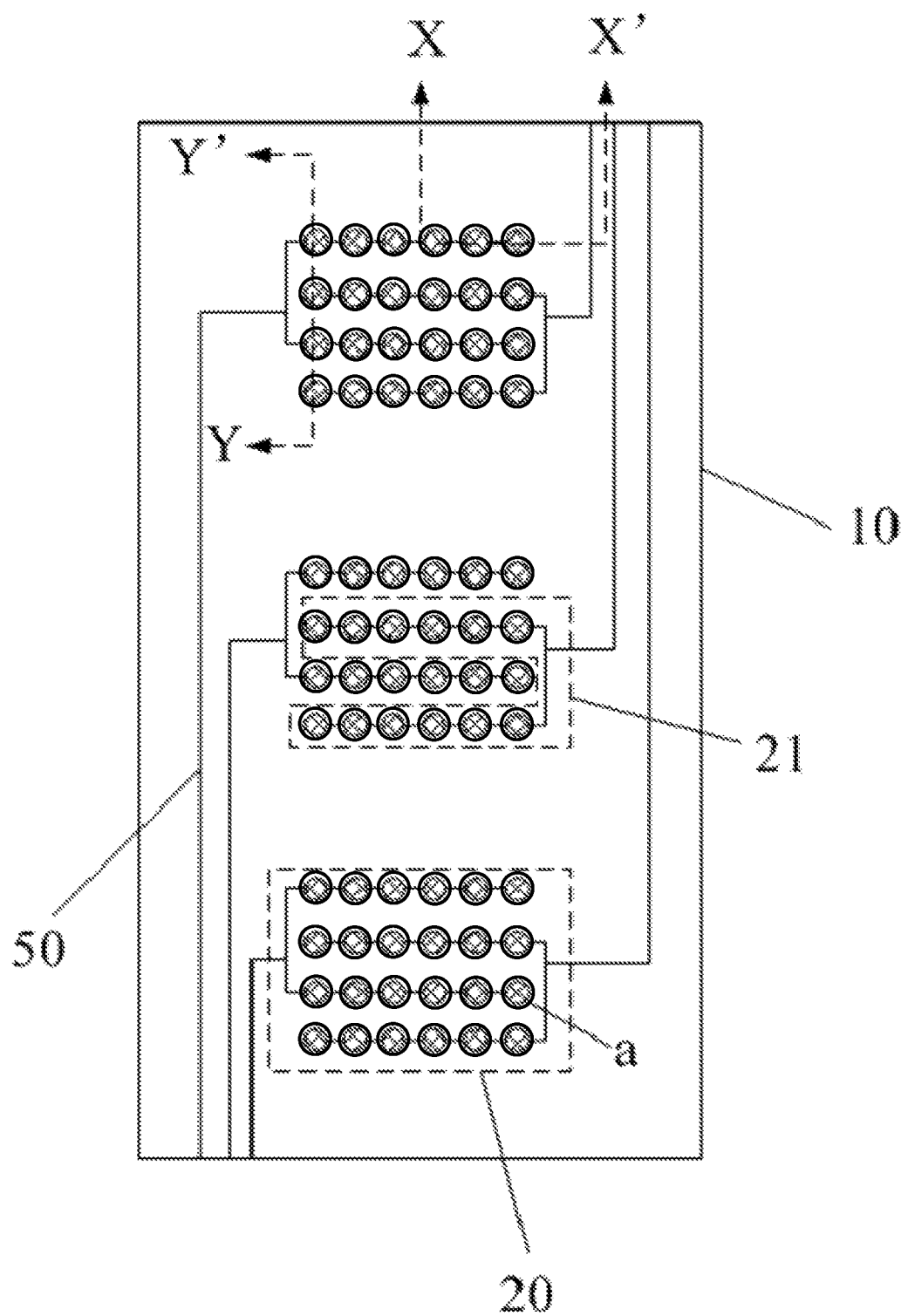
FIG. 2 is a top view of a medical detection substrate provided by an embodiment of the present disclosure.

Embodiments of the present disclosure provide a medical detection substrate, in a top view as illustrated in FIG. 2, the medical detection substrate may include: a substrate 10, and a detection unit 20 located on the substrate 10.

The detection unit 20 includes at least two groups of test electrodes. The test electrodes in a dotted border 21 in FIG. 2 refer to a group of test electrodes, another group of test electrodes is spaced apart from this group of test electrodes.

Figure 3:
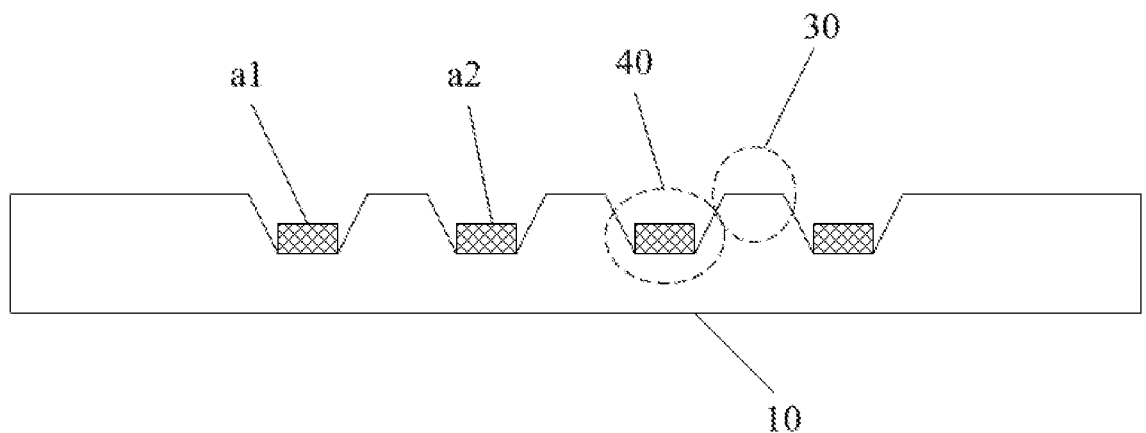
FIG. 3 is a sectional view taken along a dotted line Y-Y' in FIG. 2.

A sectional view taken along a dotted line Y-Y' in FIG. 2 is illustrated in FIG. 3, the two groups of test electrodes are spaced apart by insulation bank portions 30, the two groups of test electrodes are both located in recessed portions 40 surrounded by the bank portions 30. However, embodiments of the present disclosure are not limited thereto, as long as the two groups of test electrodes are spaced apart by the insulation bank portions 30 between the recessed portions, a structure of a top view of the recessed portions 40 is not limited to a closed structure surrounded by the bank portions.

In the abovementioned medical detection substrate provided by the embodiment of the present disclosure, the two groups of test electrodes are insulated and spaced apart from each other by the insulation bank portions, so as to effectively avoid a transverse interference electric field to be generated between the two groups of test electrodes, thereby effectively improving the detection accuracy and sensitivity of the medical detection substrate, and providing a reliable basis for the disease diagnosis.

In some examples, in order to transmit a detection signal outputted by the detection unit to a corresponding signal processing unit, so as to achieve the analysis and processing of the detection signal, in the abovementioned medical detection substrate provided by the embodiment of the present disclosure, as illustrated in FIG. 2, the medical detection substrate further includes: a plurality of data lines 50 respectively electrically connected with the two groups of test electrodes in the detection unit 20.

For example, each of the plurality of data lines 50 is made of at least two metal materials arranged in a layer stacked manner, and is configured to transmit a detection signal outputted by the detection unit 20.

For example, the data line may be made of two metal materials arranged in a layer stacked manner, as illustrated in FIG. 4 to FIG. 7 which are sectional views taken along a dotted line X-X' in FIG. 2. Of course, embodiments of the present disclosure are not limited thereto, the data line may also be made of three metal materials arranged in a layer stacked manner, as long as the resistance of the data line can be minimized, the conductivity can be the best, and the detection signal can be quickly and accurately transmitted to the corresponding signal processing unit. In addition, the metal used may be aluminum, molybdenum or copper, or other metals having excellent conductivity after being combined, which is not limited thereto.

For example, in the abovementioned medical detection substrate provided by the embodiments of the present disclosure, the number of the detection unit may be one, but in order to improve the detection efficiency, usually, a plurality of detection units can be provided on the medical detection substrate. As illustrated in FIG. 2, only three detection units 20 are illustrated, and a shape of the detection unit 20 may be square, circular or other shapes, which is not limited thereto.

For example, each detection unit includes two groups of test electrodes, and each group of the two groups of test electrodes may include one test electrode. However, in order to increase accuracy and sensitivity of the detection, each group of the two groups of test electrodes may include a plurality of test electrodes, as illustrated in FIG. 2. Of course, the number of the test electrodes is not limited to the number illustrated in FIG. 2. In the case that each group of the two groups of test electrodes includes a plurality of test electrodes, a position of the test electrodes and a connection structure between the test electrodes are illustrated in FIG. 2, the test electrodes in the first group is spaced apart from the test electrodes in the second group, and the test electrodes belonging to the same group are electrically connected to facilitate electric current in each test electrode to flow out.

For example, as illustrated in FIG. 2, three detection units 20 are schematically illustrated. Each detection unit 20 includes two groups of test electrodes. The test electrodes in the dotted border 21 are one group of test electrodes, the test electrodes outside the dotted border in each detection unit are another group of test electrodes.

Figure 4:
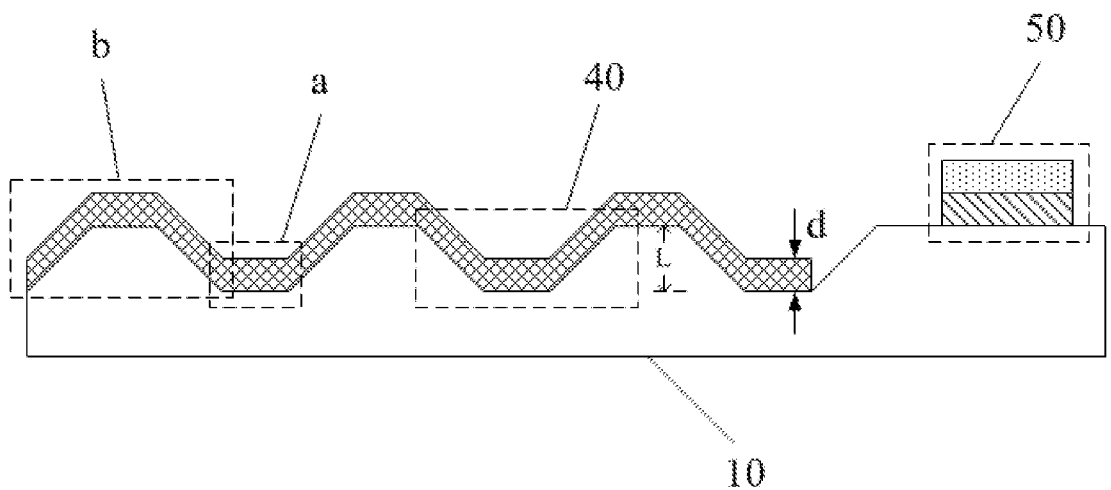
FIG. 4 to FIG. 7 are sectional views taken along a dotted line X-X' in FIG. 2.
Figure 6:
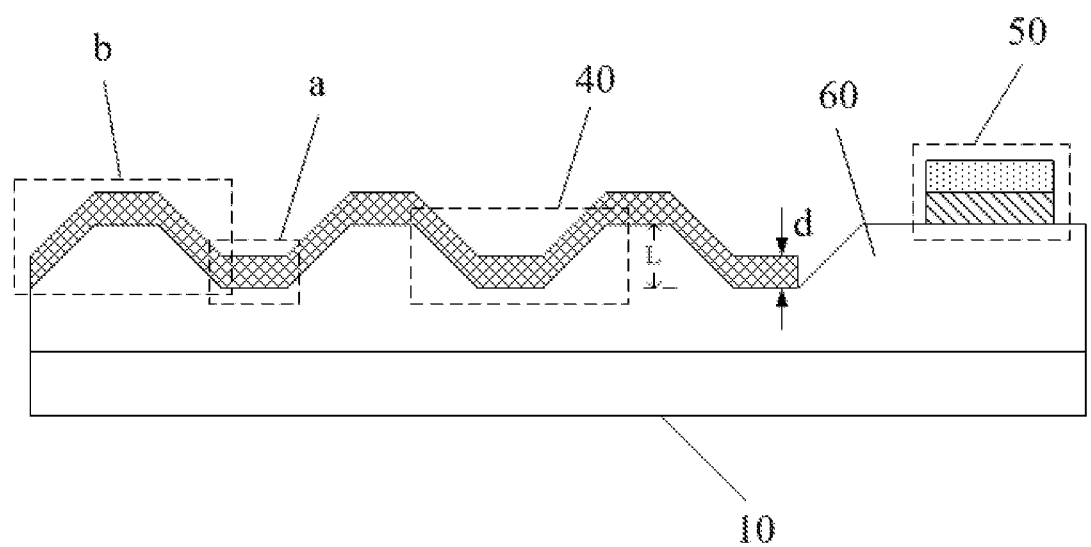

For example, in order to improve the detection accuracy of the detection unit, in the abovementioned medical detection substrate provided by the embodiments of the present disclosure, as illustrated in FIG. 2, FIG. 4 and FIG. 6, each test electrode may include a plurality of test sub-electrodes a connected in series; the test sub-electrodes a are located in the recessed portions 40, and b refers to a connection wire connecting test sub-electrodes a in one test electrode.

For example, as illustrated in FIG. 2, each group of test electrodes includes a plurality of test electrodes, and each of the plurality of test electrodes is formed by connecting a plurality of test sub-electrodes arranged in a transverse direction in FIG. 2 in series. FIG. 2 schematically illustrates that each group of test electrodes includes two test electrodes, but embodiments of the present disclosure are not limited thereto. In each group of test electrodes, the plurality of test electrodes are electrically connected with each other.

For example, in order to effectively avoid the transverse interference electric field between test sub-electrodes, in the case that the test sub-electrodes a are located in the recessed portions 40, the recessed portions 40 may be disposed in the substrate 10, or an insulation layer is located between the substrate 10 and the detection unit 20, the recessed portions 40 are located in the insulation layer. Therefore, in the abovementioned medical detection substrate provided by embodiments of the present disclosure, as illustrated in FIG. 3 to FIG. 5, the recessed portions 40 are located in the substrate 10.

Figure 7:
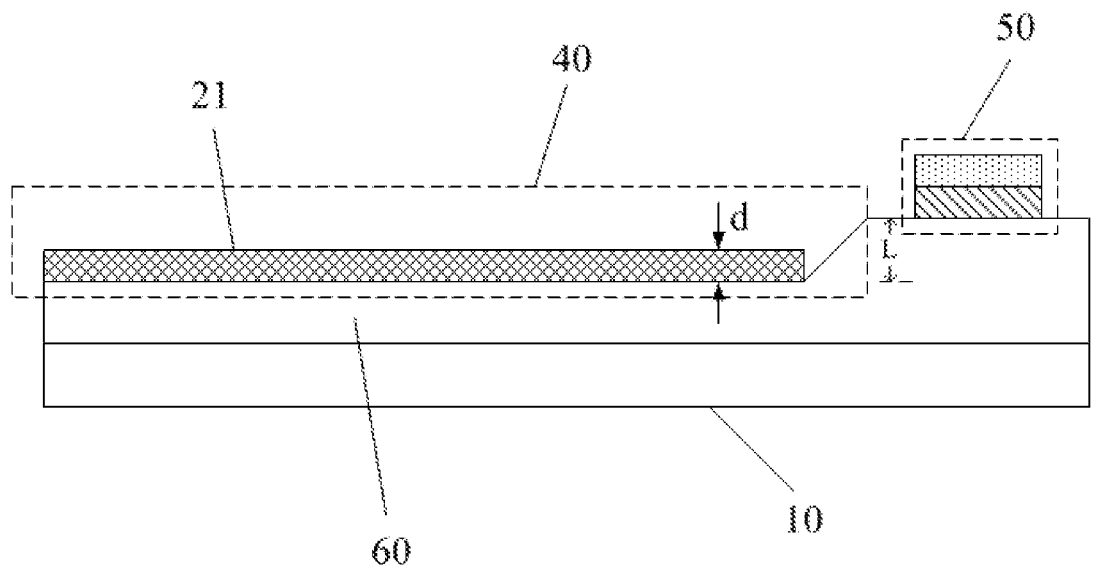

Optionally, the abovementioned medical detection substrate provided by the embodiments of the present disclosure, as illustrated in FIG. 6 and FIG. 7, further includes an insulation layer 60 located between the substrate 10 and the detection units 20. Each of the recessed portions 40 is located in the insulation layer 60.

For example, a sectional view taken along a dotted line Y-Y' in FIG. 2 is as illustrated in FIG. 3, a1 refers to a test sub-electrode in the first group of test electrodes, a2 refers to a test sub-electrode in the second group of test electrodes. Bank portions 30 of the substrate 10 are used to separate a1 and a2 to avoid a transverse electric field to be generated between a1 and a2, thereby improving the detection accuracy of the medical detection substrate. Further, a structure illustrated in FIG. 4 is taken as an example, in order to improve the detection accuracy of the medical detection substrate, an interval between adjacent recessed portions 40 can be reduced, that is, the number of the test sub-electrodes a is increased, so that the detection sensitivity of the medical detection substrate is increased. Of course, the size of the interval between the recessed portions 40 can be set according to actual process conditions, which is not limited herein.

Figure 5:
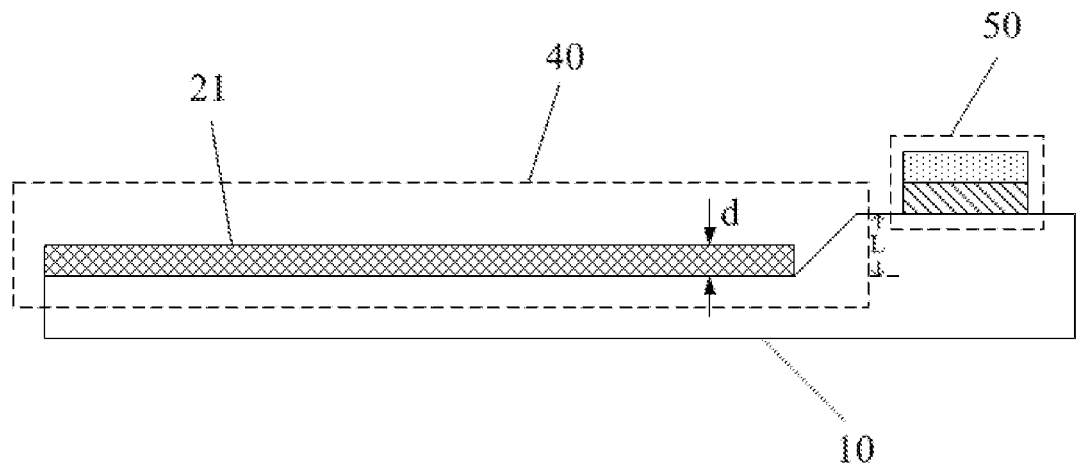

For example, in the case that test sub-electrodes belonging to different groups of test electrodes are spaced apart by the insulation bank portions, in the abovementioned medical detection substrate provided by the embodiments of the present disclosure, as illustrated in FIG. 5 and FIG. 7, the recessed portions 40 are in a one-to-one correspondence with the test electrodes 21. That is, the test sub-electrodes a belonging to one test electrode are located in one recessed portion 40. That is to say, each test sub-electrode a and each connection wire are located in the recessed portion. Optionally, as illustrated in FIG. 4 and FIG. 6, the recessed portions 40 are in a one-to-one correspondence with the test sub-electrodes a, that is, the test sub-electrodes a belonging to one test electrode are respectively located in different recessed portions 40, and the wires connecting adjacent test sub-electrodes are at least partially located on the bank portions between adjacent recessed portions.

For example, in the case that the recessed portions 40 are in a one-to-one correspondence with the test sub-electrodes a, that is, the test sub-electrodes a are located in different recessed portions 40, as illustrated in FIG. 4 and FIG. 6, in order to allow the test sub-electrodes a in one test electrode to be electrically connected, it is necessary to provide a connection wire b on a surface of the insulation bank portion between two test sub-electrodes a to realize the output of the detection signal.

For example, in the structure as illustrated in FIG. 4 to FIG. 7, in order to space apart the test sub-electrodes by the bank portion, in the abovementioned medical detection substrate provided by the embodiments of the present disclosure, a depth L of each recessed portion 40 is greater than a thickness d of each test sub-electrode, so that each test sub-electrode is completely inside the recessed portion 40, the test sub-electrodes are effectively spaced apart by the bank portions, thereby effectively avoiding the transverse interference electric field to be generated, and increasing the detection accuracy of the medical detection substrate.

For example, in the abovementioned medical detection substrate provided by the embodiments of the present disclosure, the depth L of the recessed portion is generally between 10 microns and 100 microns, and the thickness d of the test sub-electrode is generally between 100 nm and 500 nm.

Further, although each test sub-electrode is a conductor, the thinner the thickness of the test sub-electrode is, the larger the sheet resistance of the test sub-electrode is, and the conductivity of the test sub-electrode is deteriorated, resulting in a decrease in sensitivity of the medical detection substrate. Therefore, in order to allow the medical detection substrate to have a high sensitivity, in the abovementioned medical detection substrate provided by the embodiments of the present disclosure, each test sub-electrode has a sheet resistance generally ranging from 10Ω/□ to 200Ω/□.

For example, in order to use the medical detection substrate for actual medical detection, and provide a favorable reference for a doctor, after above medical detection substrate is obtained, it is also necessary to sequentially form a conductive layer, a substrate for growing a DNA target material, and a DNA target material on the medical detection substrate. Therefore, in order to allow the test sub-electrode and the conductive layer to be in a better contact and allow the detection signal to be transmitted better, in the abovementioned medical detection substrate provided by the embodiments of the present disclosure, each test sub-electrode is made of indium tin oxide or inert metal.

Further, in the case that each test sub-electrode is in a layer stacked structure, the detection sensitivity of the test sub-electrode is greatly reduced. Therefore, in the abovementioned medical detection substrate provided by the embodiments of the present disclosure, each test sub-electrode is generally provided as a single layer and composed of one material; and it has been found through experiments that upon the medical detection chip manufactured by the abovementioned medical detection substrate provided by the embodiments of the present disclosure being used to determine the final result whether negative or positive, the output of the negative signal is increased, thereby improving the detection accuracy.

Based on the same inventive concept, in order to obtain the abovementioned medical detection substrate provided by the embodiments of the present disclosure, embodiments of the present disclosure further provide a manufacturing method of the abovementioned medical detection substrate provided by the embodiments of the present disclosure, the method may include: forming recessed portions configured to receive test electrodes; forming the test electrodes in the recessed portions; forming two groups of test electrodes by alternately electrically connecting the test electrodes, the test electrodes being spaced apart; and the two groups of test electrodes forming a detection unit.

In the abovementioned manufacturing method provided by the embodiments of the present disclosure, the two groups of test electrodes are insulated and spaced apart by insulation bank portions for forming the recessed portions, thereby effectively avoiding a transverse interference electric field to be generated between the two groups of test electrodes, and effectively improving the detection accuracy and sensitivity of the medical detection substrate. Meanwhile, the manufacturing method of the medical detection substrate is simple, and mass production can be performed, therefore, the production efficiency of the medical detection substrate is improved while the medical detection substrate has excellent detection performance.

For example, the abovementioned manufacturing method provided by the embodiments of the present disclosure may further include: forming data lines electrically connected with each group of the two groups of test electrodes, each of the data lines is made of at least two metals arranged in a layer stacked manner.

For example, in the abovementioned manufacturing method provided by the embodiments of the present disclosure, forming the recessed portions configured to receive the test electrodes may include: forming an insulation layer on the substrate; and forming the recessed portions and the bank portions in the insulation layer by a patterning process.

For example, in the abovementioned manufacturing method provided by the embodiments of the present disclosure, forming the recessed portions configured to receive the test electrodes may include: forming the recessed portions and the bank portions on the substrate by an etching process.

For example, because each group of the two groups of test electrodes includes a plurality of test sub-electrodes connected in series, and the test sub-electrodes are electrically connected, each of the test sub-electrodes and connection wires connecting adjacent ones of the test sub-electrodes scan be simultaneously manufactured, that is, they are manufactured in one patterning process, so as to reduce the number of masks and simplify the manufacturing process. Of course, because each of the test sub-electrodes is made of indium tin oxide (ITO) or inert metal, the cost is much, and the connection wire is only used for conducting electricity, the material of the connection wire can be an ordinary metal. Thus, in order to reduce the manufacturing cost, the test sub-electrodes and the connection wire connecting adjacent test sub-electrodes can be separately manufactured, which is not limited herein.

The abovementioned manufacturing method provided by the embodiments of the present disclosure will be described below in detail with reference to some embodiments.

According to the structure illustrated in FIG. 4, the steps of the abovementioned manufacturing method provided by the embodiments of the present disclosure are as follows: forming recessed portions and bank portions on a substrate by an etching process.

Figure 8A:
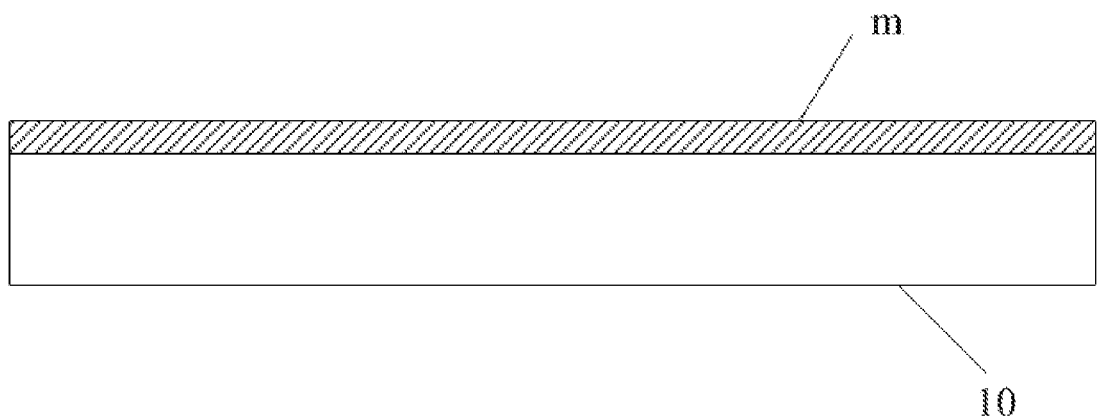
FIG. 8a to FIG. 8e are schematic views of a structure of a medical detection substrate provided by an embodiment of the present disclosure in a manufacturing process.
Figure 8B:
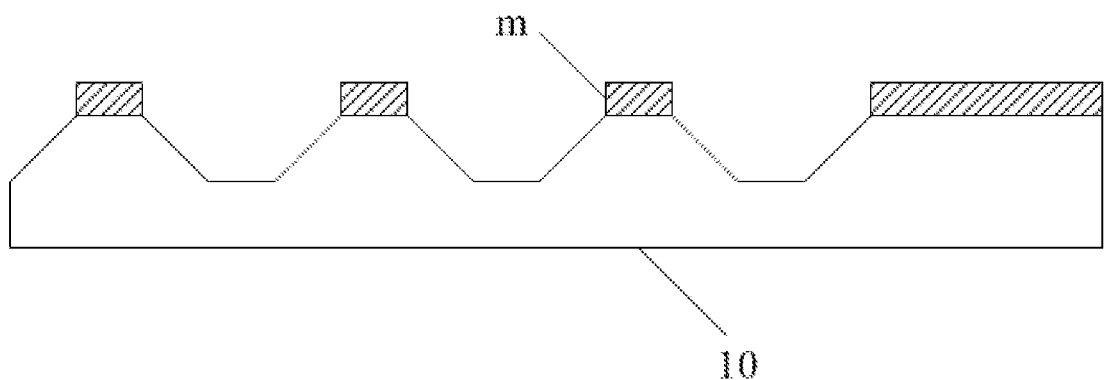
Figure 8C:
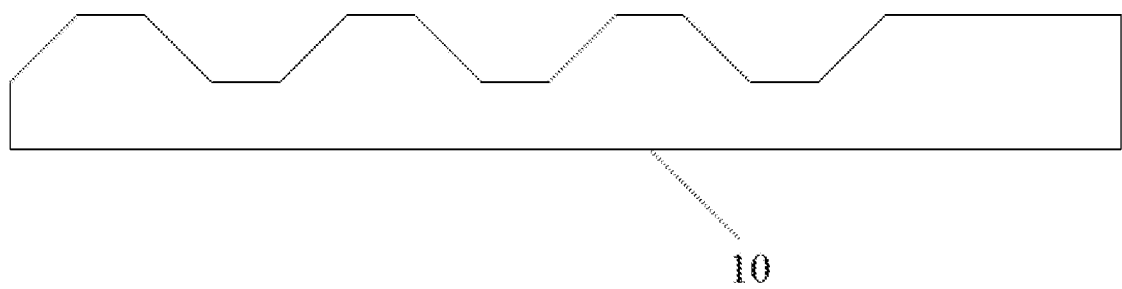

For example, as illustrated in FIG. 8a, firstly, a first mask layer m is deposited on the substrate 10, and the first mask layer m may be made of a metal or an insulation material; as illustrated in FIG. 8b, then, the bank portions and the recessed portions are formed on the substrate 10 by an etching process with a mask; as illustrated in FIG. 8c, and then, a remaining portion of the first mask layer m is removed to form the substrate 10 having the recessed portions.

The method further includes: forming test sub-electrodes in the recessed portions, a plurality of test sub-electrodes being connected in series to form a test electrode; alternately electrically connecting the test electrodes to form two groups of test electrodes, the test electrodes being spaced apart; and the two groups of test electrodes forming a detection unit.

Figure 8D:
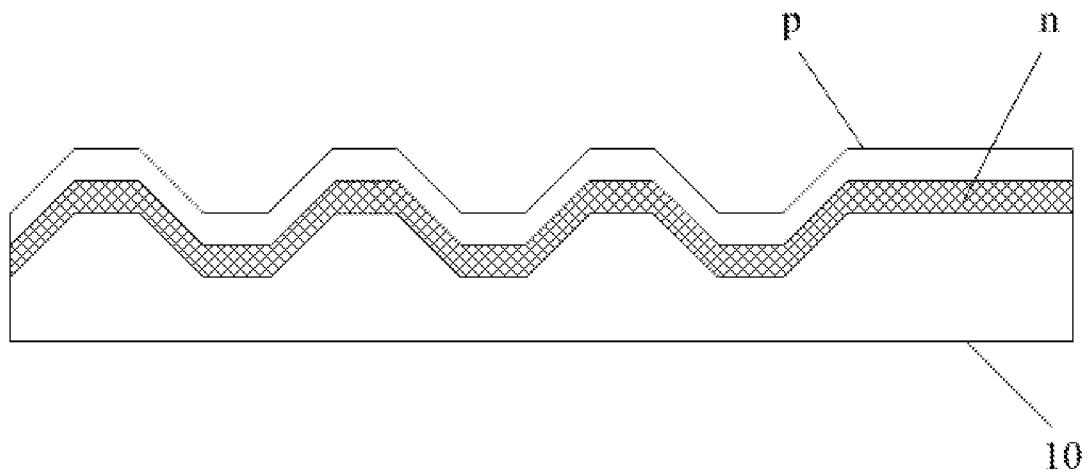
Figure 8E:
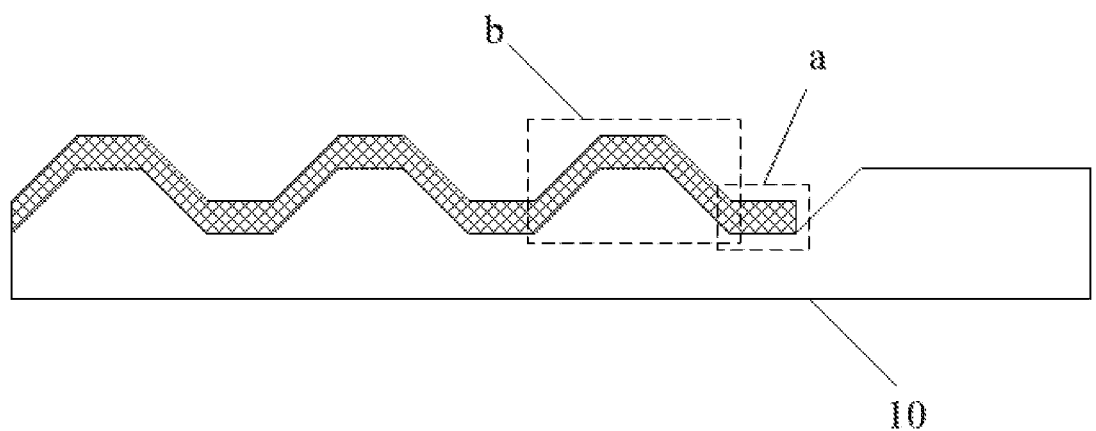

For example, as illustrated in FIG. 8d, firstly, a conductive layer n for forming test sub-electrodes, and photoresist p are sequentially deposited on the substrate 10 on which the recessed portions are formed. As illustrated in FIG. 8e, the test sub-electrodes are formed in the recessed portions respectively, connection wires are formed between the test sub-electrodes belonging to the same test electrode to form each test electrode, and wires for connecting the test electrodes spaced apart is formed by a patterning process, and finally a detection unit is formed. However, FIG. 8e only illustrates locations of each test sub-electrode a and a part of the connection wires b.

A data line configured to electrically connected to each group of the at least two groups of test electrodes is made of at least two metals arranged in a layer stacked manner.

For example, the data lines are formed on opposite sides of the detection unit by the same process as forming the detection unit, so as to finish the production of the medical detection chip, and the repeated portion is omitted here.

According to the structure as illustrated in FIG. 6, the steps of the abovementioned manufacturing method provided by the embodiments of the present disclosure are as follows: forming an insulation layer on a substrate; forming bank portions and recessed portions in the insulation layer by a patterning process; forming test sub-electrodes in the recessed portions; forming a test electrode by connecting a plurality of test sub-electrodes in series; forming two groups of test electrodes by electrically alternately connecting the test electrodes, the test electrodes being spaced apart (that is, different test electrodes are spaced apart, and the test electrodes in the same group are electrically connected with each other); forming a detection unit by the two groups of test electrodes; forming a data line electrically connected with each group of the two groups of test electrodes, the data line being made of at least two metals arranged in a layer stacked manner.

For example, in the abovementioned manufacturing method, firstly, an insulation layer 60 is deposited on the substrate; and then, the bank portions and the recessed portions are formed in the insulation layer 60 by a patterning process to form the insulation layer 60 having the recessed portions, as illustrated in FIG. 6. The process of fabricating the detection unit and the data line is similar to the process illustrated in FIG. 8d and FIG. 8e, and the repeated portion is omitted here.

Based on the same inventive concept, embodiments of the present disclosure further provide a medical detection chip, which may include: the abovementioned medical detection substrate provided by any one of the embodiments of the present disclosure and a labeled detection reagent located on the medical detection substrate.

Figure 9A:
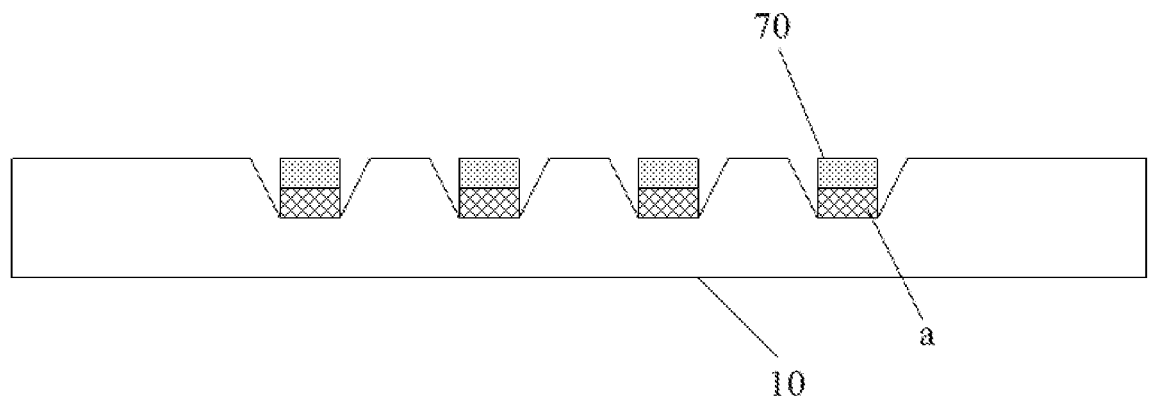
FIG. 9a to FIG. 9e are schematic views of a structure of a medical detection substrate provided by an embodiment of the present disclosure in a packaging process.
Figure 9B:
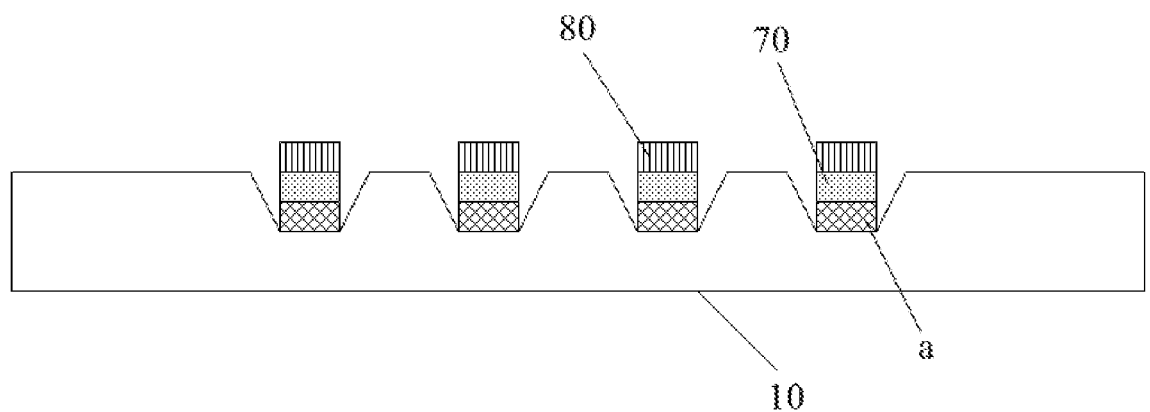
Figure 9C:
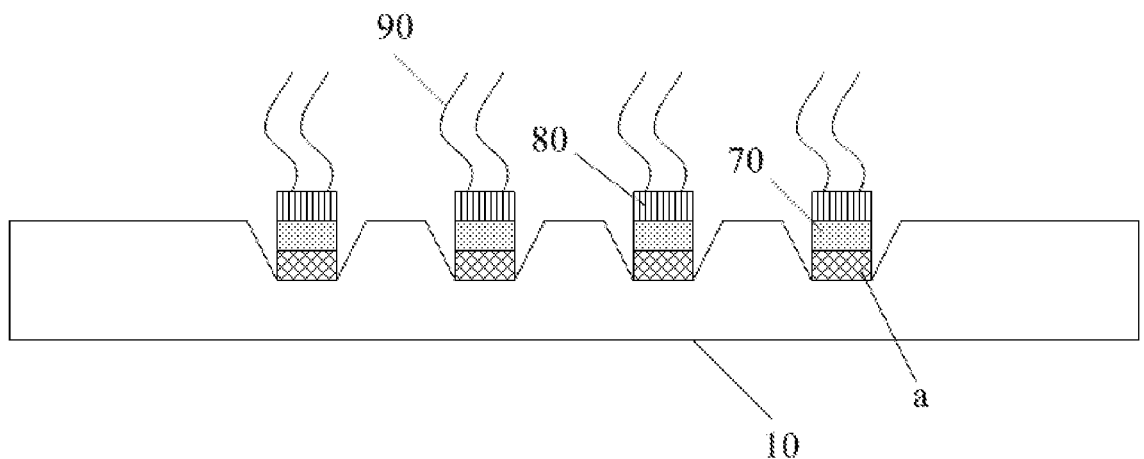
Figure 9D:
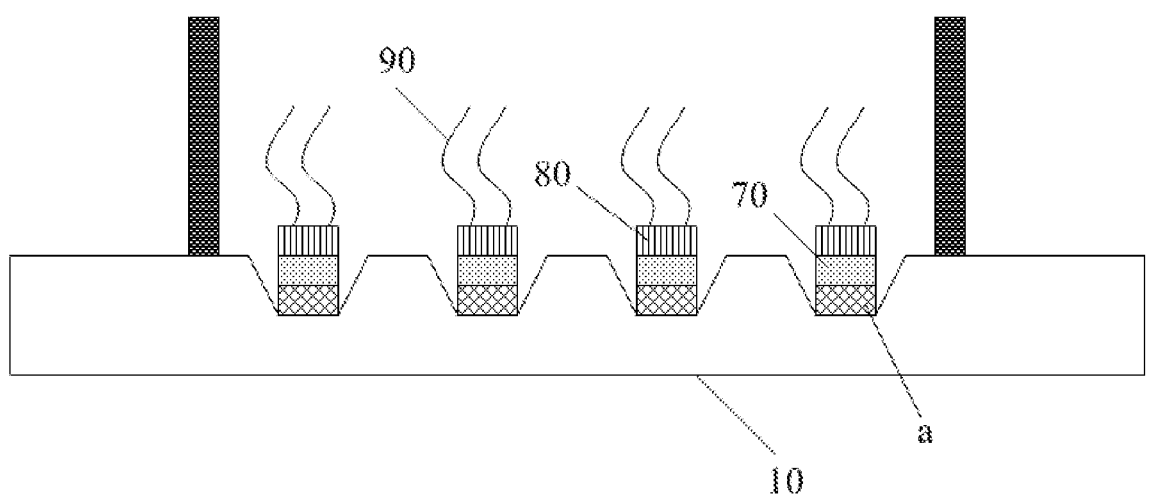
Figure 9E:
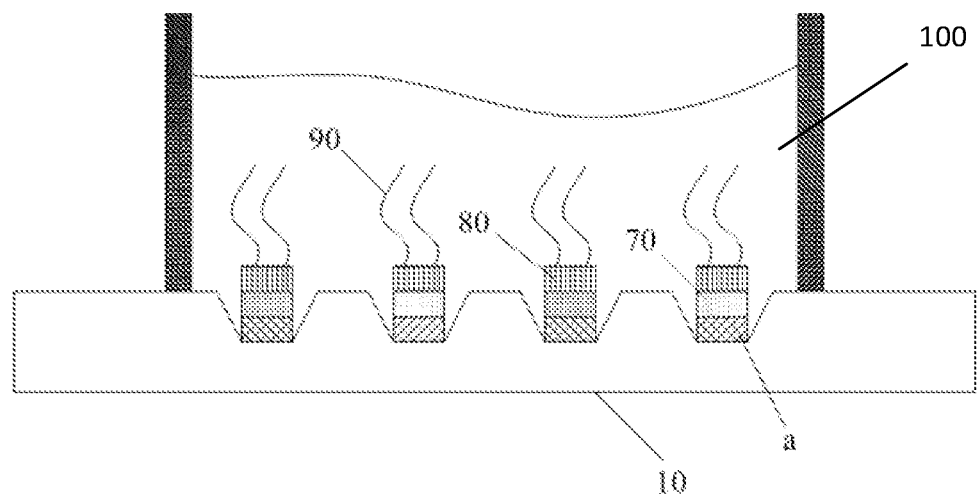

For example, in order to allow the medical detection chip to be used for actual disease detection, in combination with the structure illustrated in FIG. 3, after the above medical detection substrate is completed, the following steps are also performed: as illustrated in FIG. 9a, forming a conductive layer 70 on a surface of each test sub-electrode a in the detection unit; as illustrated in FIG. 9b, growing a DNA target substrate 80 on the conductive layer 70; as illustrated in FIG. 9c, growing a DNA paired target 90 on the DNA target substrate 80; as illustrated in FIG. 9d, packaging the detection unit in which the DNA paired target 90 has been grown; as illustrated in FIG. 9e, pouring liquid 100 to be tested into the packaged detection unit for DNA detection. However, the embodiments of the present disclosure are not limited thereto, and other labeled detection reagents can be disposed on the medical substrate for detection of other uses.

It should be understood that, a sum of a thickness of the conductive layer 70 and the test sub-electrode a is not greater than a depth of each of the recessed portions. That is, the conductive layer 70 and the test sub-electrode a are located in the recessed portion, conductive portions composed of the conductive layer 70 and the test sub-electrode a are insulated and spaced apart by the bank portions to avoid a transverse interference electric field to be generated between the conductive portions, thereby preventing the detection result from being interfered. FIG. 9a to FIG. 9e only illustrate that the sum of the thickness of the conductive layer 70 and the test sub-electrode a is equal to the depth of the recessed portion, but the embodiment is not limited thereto.

For example, the medical detection substrate after being packaged and illustrated in FIG. 9e is a sectional view taken along line Y-Y' in FIG. 2. In combination with the structure illustrated in FIG. 5, when taken along line X-X' in FIG. 2, a sectional view of the medical detection substrate after being packaged is illustrated in FIG. 10, in this case, because the test electrode 21 corresponds to one recessed portion, and different portions of the test electrode 21 have the same electric potential, in the packaging process, the conductive layer 70 and the DNA target substrate 80 may completely cover a surface of one test electrode 21, so as to simplify the production process.

Figure 10:
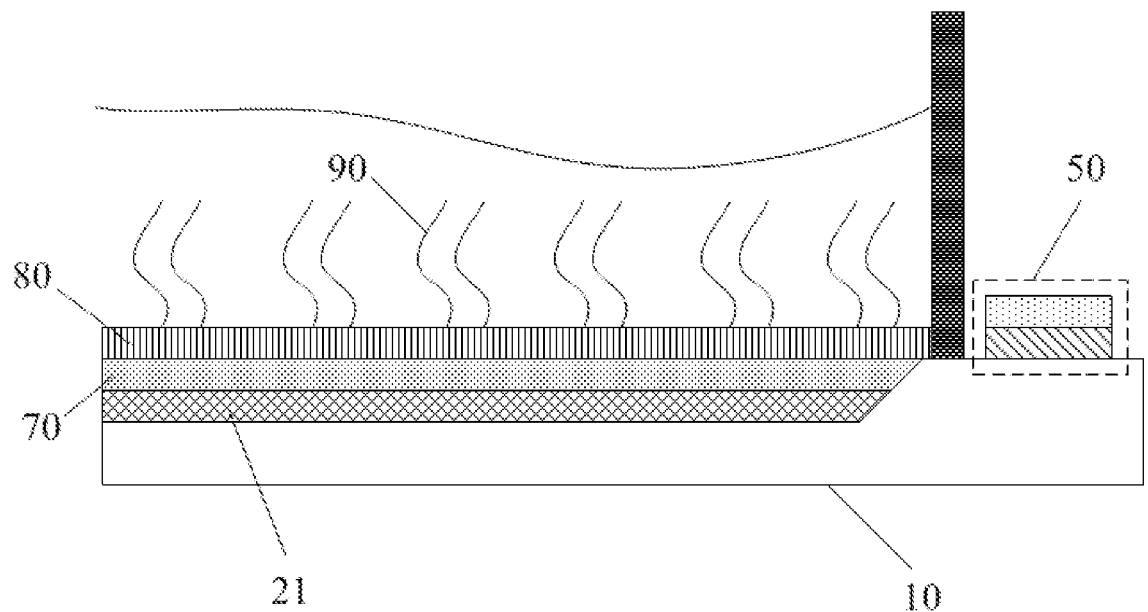
FIG. 10 and FIG. 11 are sectional views of a medical detection substrate, provided by an embodiment of the present disclosure, after being packaged.

Of course, in FIG. 10, it is also possible to omit the fabrication of the conductive layer 70 (which is not illustrated in figures). In this case, it is only necessary to select the material of the test electrode as a material compatible with the DNA target substrate, thereby, in the case of being used normally, simplifying the manufacturing process and reducing the manufacturing cost.

Figure 11:
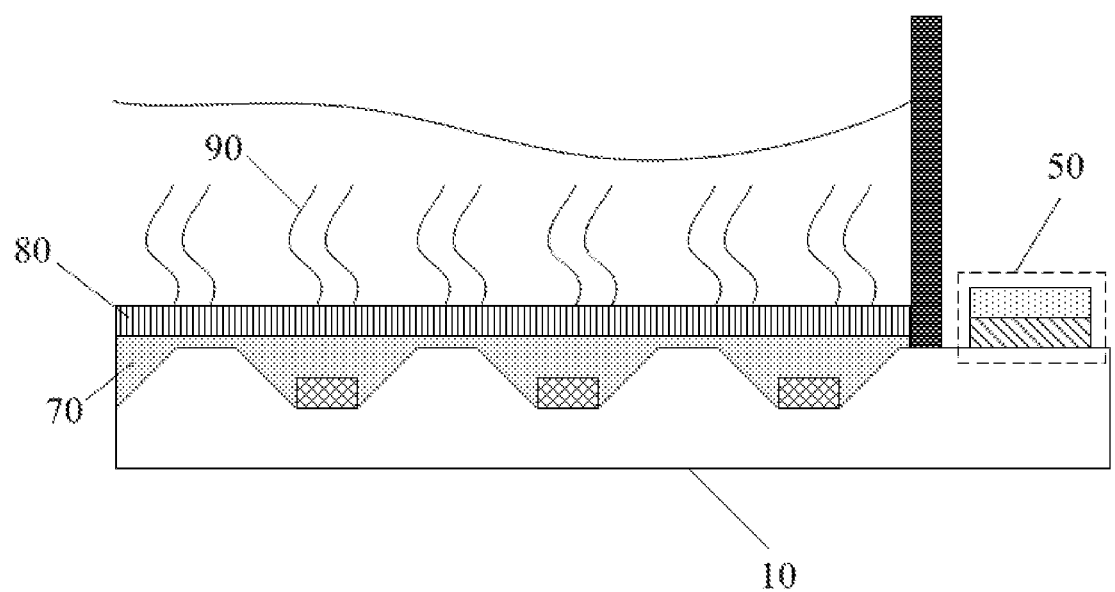

For example, when the medical detection substrate illustrated in FIG. 4 is packaged, in order to simplify the process and reduce the manufacturing cost, when forming the medical detection substrate, only the test sub-electrodes are formed in the recessed portions without forming wires connecting the test sub-electrodes. Then, a conductive layer 70 is deposited on a surface of each test sub-electrode and the bank portions between the test sub-electrodes belonging to one test electrode for achieving electrical connection of each test sub-electrode, and at the same time for fabricating the DNA target substrate thereon, which is specifically illustrated in FIG. 11.

Figure 12:
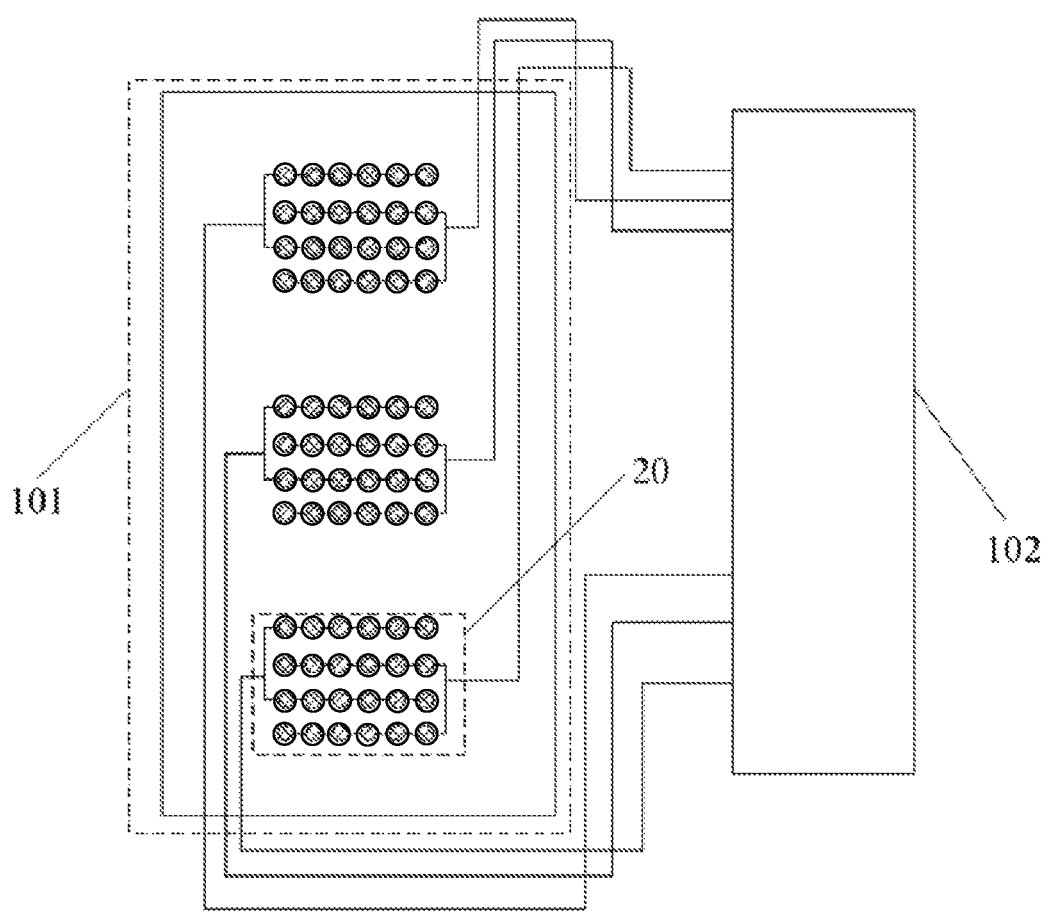
FIG. 12 is a schematic view of a structure of a medical detection system provided by an embodiment of the present disclosure.

Base on the same inventive concept, embodiments of the present disclosure further provide a medical detection system, as illustrated in FIG. 12, the system may include: the abovementioned medical detection chip 101 provided by the embodiments of the present disclosure, and a signal processing unit 102 configured to process a detection signal outputted by the detection unit 20 in the medical detection chip 101.

For example, the signal processing unit 102 and each detection unit 20 are electrically connected by wires to transmit the detection signal outputted by the detection unit 20 to the signal processing unit 102. The detection signal is analyzed and processed by the signal processing unit to achieve a corresponding result and provide a favorable basis for disease detection.

In the embodiments of the present disclosure, the signal processing unit can be implemented in software for execution by various types of processors. For example, an identified executable code module may include one or more physical or logical blocks of computer instructions, for example, the identified executable code module may be built as an object, procedure, or function. However, the executable codes of the identified module need not to be physically located together, but may include different instructions stored in different physical locations. Upon being logically combined, the instructions form a module and achieve a specified purpose of the module.

In fact, the executable code module may include a single instruction or a plurality of instructions, and may even be distributed in different code segments, distributed in different programs, and distributed in a plurality of memory devices. Similarly, operational data may be identified within the modules and may be implemented in any suitable form and organized within any suitable type of data structure. The operational data may be collected as a single data set, or may be distributed at different locations (including in different storage devices), and may at least partially exist only as an electronic signal on a system or network.

In the case that the signal processing unit is implemented by software, considering the level of the existing hardware process, for the module that may be implemented by software, those skilled in the art can build a corresponding hardware circuit to implement corresponding functions without considering the cost. The hardware circuit includes a conventional very large scale integration (VLSI) circuit or a gate array, and an existing semiconductor such as a logic chip, a transistor, or other separated components. The module can also be implemented with a programmable hardware device such as a field programmable gate array device, a programmable array logic device, a programmable logic device, or the like.

Embodiments of the present disclosure further provide a manufacturing method of a medical detection substrate, which includes: forming a plurality of recessed portions on a substrate; forming at least two groups of test electrodes in the plurality of recessed portions. The at least two groups of test electrodes are spaced apart by insulation bank portion s between the plurality of recessed portions.

In some examples, the method further includes: before forming the plurality of recessed portions on the substrate, forming an insulation layer on the substrate, the recessed portion being formed in the insulation layer. In other examples, the recessed portion is directly formed in the substrate.

For example, a process of forming the recessed portions may use any suitable patterning process. For example, a photoresist pattern may be formed on the substrate firstly, and then the abovementioned recessed portions are formed by an etching process with the photoresist pattern as a mask. In addition, a way for forming the abovementioned test electrode is not particular limited. For example, a material layer for forming the test electrode may be formed on the substrate firstly, and then the material layer is patterned to allow the test electrodes to be formed in the recessed portions.

For example, a depth of each of the recessed portions is greater than a thickness of each of the test sub-electrodes.

The positional relationship and the size of each structure in the manufacturing method of the medical detection substrate in the embodiment can refer to the related description of the abovementioned medical detection substrate in the embodiments.

The embodiments of the present disclosure provide a medical detection substrate and a manufacturing method thereof, a medical detection chip and a medical detection system. The medical detection substrate includes: a substrate, and a detection unit on the substrate. The detection unit includes two groups of test electrodes, the two groups of test electrodes are spaced apart by insulation bank portions, and the two groups of test electrodes are disposed in recessed portions surrounded by the bank portions. Therefore, the two groups of test electrodes are insulated and spaced apart by the insulation bank portions, so as to effectively avoid a transverse interference electric field to be generated between the two groups of test electrodes, thereby effectively improving the detection accuracy and sensitivity of the medical detection substrate, and providing a reliable basis for disease diagnosis.

The above are merely exemplary embodiments of the present disclosure, and are not intended to limit the scope of the present disclosure. The scope of the present disclosure is defined by the appended claims.

The present application claims the benefit of priority from Chinese patent application No. 201710595582.6 filed on Jul. 20, 2017, the disclosure of which is incorporated herein in its entirety by reference as a part of the present application.

What is claimed is:

1. A medical detection substrate, comprising:
a substrate; and
a detection unit, located on the substrate, the detection unit comprising at least two groups of test electrodes,
wherein the medical detection substrate further comprises a plurality of recessed portions, and the at least two groups of test electrodes are located in the plurality of recessed portions and spaced apart by insulation bank portions,
the medical detection substrate further comprises an insulation layer located between the substrate and the detection unit, wherein the plurality of recessed portions are located in the insulation layer.

2. The medical detection substrate according to claim 1, wherein the plurality of recessed portions are located in the substrate.

3. The medical detection substrate according to claim 1, wherein each group of the at least two groups of test electrodes comprises at least one test electrode, each test electrode comprises a plurality of test sub-electrodes connected in series, and
the plurality of test sub-electrodes are located in the plurality of recessed portions.

4. The medical detection substrate according to claim 3, wherein the plurality of test sub-electrodes connected in series in each test electrode are electrically connected by wires.

5. The medical detection substrate according to claim 4, wherein the plurality of recessed portions are in a one-to-one correspondence with the test electrodes, the plurality of test sub-electrodes and the wires are located in the plurality of recessed portions; or, the plurality of recessed portions are in a one-to-one correspondence with the plurality of test sub-electrodes, at least a part of the wires between adjacent ones of the test sub-electrodes is located on the bank portions between the plurality of recessed portions.

6. The medical detection substrate according to claim 3, wherein each group of the at least two groups of test electrodes comprises at least two test electrodes, the at least two test electrodes in each group of the at least two groups of test electrodes are electrically connected with each other.

7. The medical detection substrate according to claim 6, wherein the test electrodes in the at least two groups of test electrodes are alternately arranged.

8. The medical detection substrate according to claim 3, wherein a depth of each of the plurality of recessed portions is greater than a thickness of each of the plurality of test sub-electrodes.

9. The medical detection substrate according to claim 8, wherein the depth of the recessed portion is between 10 microns and 100 microns, and
the thickness of the test sub-electrode is between 100 nm and 500 nm.

10. The medical detection substrate according to claim 3, wherein each of the plurality of test sub-electrodes has a sheet resistance ranging from $10\Omega/\square$ to $200\Omega/\square$.

11. The medical detection substrate according to claim 10, wherein each of the plurality of test sub-electrodes is made of indium tin oxide or inert metal.

12. The medical detection substrate according to claim 1, further comprising: a plurality of data lines respectively electrically connected with the at least two groups of test electrodes in the detection unit,
wherein each of the plurality of data lines is made of at least two metal materials arranged in a layer stacked manner, and the data line is configured to transmit a detection signal outputted by the detection unit.

13. The medical detection substrate according to claim 1, further comprising: a DNA target substrate located above the at least two groups of test electrodes and a DNA paired target located above the DNA target substrate.

14. A medical detection chip, comprising:
the medical detection substrate according to claim 1; and
a labeled detection reagent on the medical detection substrate.

15. A medical detection system, comprising: the medical detection chip according to claim 14; and
a signal processor configured to process a detection signal outputted by the detection unit in the medical detection chip.

16. A manufacturing method of a medical detection substrate, comprising:
forming a plurality of recessed portions on a substrate; and
forming at least two groups of test electrodes in the plurality of recessed portions,
wherein the at least two groups of test electrodes are spaced apart by insulation bank portions between the plurality of recessed portions,
before forming the plurality of recessed portions on the substrate, the method further comprises: forming an insulation layer on the substrate, wherein the plurality of recessed portions are formed in the insulation layer, wherein the insulation layer is located between the substrate and the at least two groups of test electrodes, and the plurality of recessed portions are located in the insulation layer.

17. The method according to claim 16, wherein each group of the at least two groups of test electrodes comprises at least one test electrode, each test electrode comprises a plurality of test sub-electrodes connected in series, and the plurality of test sub-electrodes are located in the plurality of recessed portions, and a depth of each of the plurality of recessed portions is greater than a thickness of each of the plurality of test sub-electrodes.

18. The method according to claim 16, wherein the insulation bank portions and the plurality of recessed portions are formed in a same patterning process.

* * * * *